(12) United States Patent
Thenuwara et al.

(10) Patent No.: US 8,915,926 B2
(45) Date of Patent: Dec. 23, 2014

(54) PRE-CURVED ELECTRODE ARRAY LOADING TOOLS

(75) Inventors: Chuladatta Thenuwara, Castaic, CA (US); William G. Orinski, Newbury Park, CA (US); Janusz A. Kuzma, Parker, CO (US); Steve J. Blomquist, Tucson, AZ (US)

(73) Assignee: Advanced Bionics AG, Staefa (CH)

( * ) Notice: Subject to any disclaimer, the term of this patent is extended or adjusted under 35 U.S.C. 154(b) by 550 days.

(21) Appl. No.: 11/933,861

(22) Filed: Nov. 1, 2007

(65) Prior Publication Data

US 2008/0109011 A1     May 8, 2008

Related U.S. Application Data

(60) Provisional application No. 60/858,087, filed on Nov. 8, 2006, provisional application No. 60/925,526, filed on Apr. 20, 2007.

(51) Int. Cl.
| | | |
|---|---|---|
| *A61B 19/00* | (2006.01) | |
| *A61N 1/05* | (2006.01) | |
| *A61B 17/34* | (2006.01) | |
| *A61N 1/36* | (2006.01) | |

(52) U.S. Cl.
CPC ........... *A61N 1/0541* (2013.01); *A61B 17/3468* (2013.01); *A61N 1/36032* (2013.01)
USPC ........... 606/129; 604/174; 607/126; 607/127; 607/137; 600/373; 600/393

(58) Field of Classification Search
USPC .................... 606/129; 607/91, 126, 127, 137; 600/373, 393
See application file for complete search history.

(56) References Cited

U.S. PATENT DOCUMENTS

| | | |
|---|---|---|
| 4,819,647 A | 4/1989 | Byers et al. |
| 4,898,183 A | 2/1990 | Kuzma |
| 5,314,411 A * | 5/1994 | Bierman et al. ............... 604/174 |
| 5,443,493 A | 8/1995 | Byers et al. |

(Continued)

FOREIGN PATENT DOCUMENTS

| | | |
|---|---|---|
| EP | 0109304 | 5/1984 |
| EP | 0328597 | 8/1989 |

(Continued)

OTHER PUBLICATIONS

International Search Report and Written Opinion received in International Application No. PCT/US2007/083428, May 20, 2008.

(Continued)

*Primary Examiner* — Victor Nguyen
*Assistant Examiner* — Kevin Everage
(74) *Attorney, Agent, or Firm* — ALG Intellectual Property, LLC

(57) ABSTRACT

Exemplary loading tools configured to facilitate loading of a pre-curved electrode array onto a stylet include a docking assembly, a channel assembly, and a connecting member configured to connect the channel assembly to the docking assembly and maintain a distance therebetween. The docking assembly is configured to couple to the stylet. The channel assembly includes a channel configured to receive and allow passage therethrough of the pre-curved electrode array. The channel is aligned with the docking assembly such that when the stylet is coupled to the docking assembly, the stylet is located at least partially within the channel.

13 Claims, 16 Drawing Sheets

(56) References Cited

U.S. PATENT DOCUMENTS

| | | |
|---|---|---|
| 5,667,514 A | 9/1997 | Heller |
| 6,070,105 A | 5/2000 | Kuzma |
| 6,125,302 A | 9/2000 | Kuzma |
| 6,129,753 A | 10/2000 | Kuzma |
| 6,149,657 A | 11/2000 | Kuzma |
| 6,195,586 B1 | 2/2001 | Kuzma |
| 6,219,580 B1 | 4/2001 | Faltys et al. |
| 6,272,382 B1 | 8/2001 | Faltys et al. |
| 6,308,101 B1 | 10/2001 | Faltys et al. |
| 6,421,569 B1 | 7/2002 | Treaba et al. |
| 6,604,283 B1 | 8/2003 | Kuzma |
| 6,968,238 B1 | 11/2005 | Kuzma |
| 7,050,858 B1 | 5/2006 | Kuzma et al. |
| 7,063,708 B2 | 6/2006 | Gibson et al. |
| 7,269,461 B2 | 9/2007 | Dadd et al. |
| 2002/0111634 A1* | 8/2002 | Stoianovici et al. ......... 606/129 |
| 2003/0093139 A1 | 5/2003 | Gibson et al. |
| 2004/0243177 A1 | 12/2004 | Svehla et al. |
| 2005/0251237 A1 | 11/2005 | Kuzma et al. |
| 2005/0267555 A1 | 12/2005 | Marnfeldt et al. |
| 2006/0058861 A1 | 3/2006 | Gibson et al. |
| 2006/0241723 A1* | 10/2006 | Dadd et al. ...................... 607/57 |
| 2008/0004684 A1 | 1/2008 | Dadd et al. |
| 2008/0109011 A1 | 5/2008 | Thenuwara et al. |
| 2008/0294174 A1 | 11/2008 | Bardsley et al. |

FOREIGN PATENT DOCUMENTS

| | | |
|---|---|---|
| EP | 1233810 | 8/2002 |
| EP | 1341578 | 9/2003 |
| EP | 1370205 | 12/2003 |
| EP | 1476104 | 11/2004 |
| WO | WO-8900870 | 2/1989 |
| WO | WO-9324058 | 12/1993 |
| WO | WO-9720530 | 6/1997 |
| WO | WO-00/71063 | 11/2000 |
| WO | WO-0230507 | 4/2002 |
| WO | WO-0232498 | 4/2002 |
| WO | WO-02074211 | 9/2002 |
| WO | WO-03070133 | 8/2003 |
| WO | WO-2004012809 | 2/2004 |
| WO | WO-2008/057989 | 5/2008 |

OTHER PUBLICATIONS

International Search Report and Written Opinion received in International Application No. PCT/US2011/035541, dated Oct. 7, 2011.
International Search Report and Written Opinion received in International Application No. PCT/US2011/035539, dated Dec. 29, 2011.
Non-Final Office Action received in U.S. Appl. No. 13/696,789 dated Jan. 14, 2014.
Non-Final Office Action received in U.S. Appl. No. 12/485,427 dated Feb. 5, 2014.

* cited by examiner

PRE-CURVED ELECTRODE ARRAY LOADING TOOLS

RELATED APPLICATIONS

The present application claims priority under 35 U.S.C. §119(e) to U.S. Provisional Patent Application No. 60/858,087 by Chuladatta Thenuwara et al., filed on Nov. 8, 2006, and to U.S. Provisional Patent Application No. 60/925,526 by Chuladatta Thenuwara et al., filed on Apr. 20, 2007. The contents of both of these applications are hereby incorporated by reference in their respective entireties.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an array of electrodes may be implanted in the cochlea. The electrodes form a number of stimulation channels through which electrical stimulation pulses may be applied directly to auditory nerves within the cochlea. An audio signal may then be presented to a patient by translating the audio signal into a number of electrical stimulation pulses and applying the stimulation pulses directly to auditory nerves within the cochlea via one or more of the electrodes.

The electrode array is often implanted within the scala tympani, one of the three parallel ducts that make up the spiral-shaped cochlea. Electrode arrays that are implanted in the scala tympani typically include a thin, elongate, and flexible carrier containing several longitudinally disposed and separately connected stimulating electrode contacts. Such an electrode array is pushed into the scala tympani duct to a depth of about 18-25 mm via a surgical opening made in the round window at the basal end of the duct.

During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one electrode contact site tends to selectively activate those spiral ganglion cells and their auditory nerve fibers that are closest to that contact site.

Hence, it is often desirable for the electrode contacts to be positioned as close to the ganglion cells as possible. To this end, various pre-curved electrode arrays have been developed that have spiral-shaped resilient carriers to better conform to the shape of the scala tympani. In this manner, the electrode arrays are more apt to hug the modiolar wall after implant.

However, many pre-curved electrode arrays have to first be loaded onto a straight stylet of an insertion tool before they can be inserted into the cochlea. Current methods of loading pre-curved electrode arrays onto straight stylets are cumbersome and often result in damage to the electrode arrays as they are loaded onto the stylets.

SUMMARY

Exemplary loading tools configured to facilitate loading of a pre-curved electrode array onto a stylet include a docking assembly, a channel assembly, and a connecting member configured to connect the channel assembly to the docking assembly and maintain a distance therebetween. The docking assembly is configured to couple to the stylet. The channel assembly includes a channel configured to receive and allow passage therethrough of the pre-curved electrode array. The channel is aligned with the docking assembly such that when the stylet is coupled to the docking assembly, the stylet is located at least partially within the channel.

Methods of loading a pre-curved electrode array onto a stylet include inserting a distal tip of the stylet into a proximal portion of a lumen within the electrode array, coupling the stylet to a docking assembly such that the distal tip of the stylet is located at least partially within a channel of the loading tool, and advancing the electrode array such that the electrode array passes through the channel and is loaded onto the stylet.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Exemplary loading tools configured to facilitate loading of a pre-curved electrode array onto a stylet are described herein. An exemplary loading tool includes a docking assembly, a channel assembly, and a connecting member configured to connect the channel assembly to the docking assembly and maintain a distance therebetween. The docking assembly is configured to couple to the stylet. The channel assembly includes a channel configured to receive and allow passage therethrough of the pre-curved electrode array. The channel is aligned with the docking assembly such that when the stylet is coupled to the docking assembly, the stylet is located at least partially within the channel. In this manner, as will be described in more detail below, the electrode array may be advanced through the channel and loaded onto the stylet.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
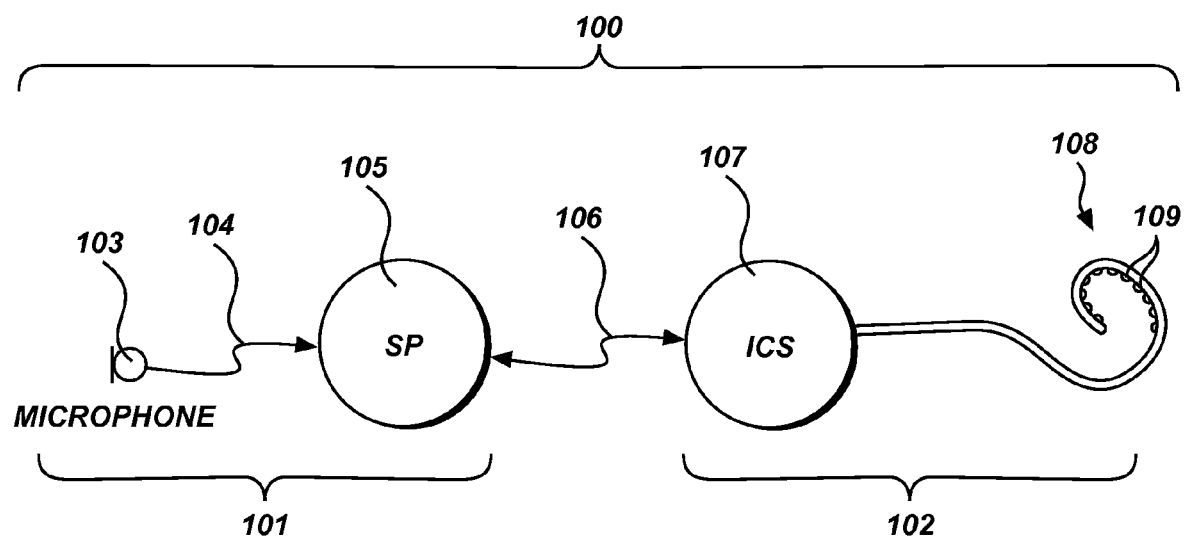
FIG. 1 illustrates an exemplary cochlear implant system according to principles described herein.

FIG. 1 illustrates an exemplary cochlear implant system 100 that may be used in accordance with the present systems and methods. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties.

The cochlear implant system 100 of FIG. 1 includes a signal processor portion 101 and a cochlear stimulation portion 102. The signal processor portion 101 may include a microphone 103, a signal processor (SP) 105, and/or additional circuitry as may serve a particular application. The cochlear stimulation portion 102 may include an implantable cochlear stimulator (ICS) 107, a pre-curved electrode array 108, and/or additional circuitry as may serve a particular application. The components within the signal processor portion 101 and the cochlear stimulation portion 102 will be described in more detail below.

The microphone 103 of FIG. 1 is configured to sense acoustic signals and convert the sensed signals to corresponding electrical signals. The electrical signals are sent from the microphone 103 to the SP 105 via a communication link 104. Alternatively, the microphone 103 may be connected directly to, or integrated with, the SP 105. The SP 105 processes these converted acoustic signals in accordance with a selected signal processing strategy to generate appropriate stimulation parameters for controlling the ICS 107. These parameters may specify or define the polarity, magnitude, location (i.e., which electrode pair or electrode group receive the stimulation current), and timing (i.e., when the stimulation current is to be applied to a particular electrode pair) of the electrical stimulation pulses that are generated by the ICS 107.

The pre-curved electrode array 108 of FIG. 1 is configured to be inserted within a duct of the cochlea. As shown in FIG. 1, the electrode array 108 includes a multiplicity of electrodes 109, e.g., sixteen electrodes, spaced along its length. It will be understood, however, that any number of electrodes 109 may be included within the electrode array 108. The electrode array 108 will be described in more detail below. Electronic circuitry within the ICS 107 is configured to generate stimulation current via selected pairs or groups of the individual electrodes 109 in accordance with a specified stimulation pattern defined by the SP 105.

The ICS 107 and the SP 105 may be electronically connected via a suitable data or communication link 106. It will be understood that the data communication link 106 may include a bidirectional communication link and/or one or more dedicated unidirectional communication links, such as the forward and back-telemetry links 103, 104 shown in FIG. 1.

In some examples, the SP 105 and the microphone 103 comprise an external portion of the cochlear implant system 100 and the ICS 107 and the electrode array 108 comprise an implantable portion of the system 100 that is implanted within a patient's body. In alternative embodiments, one or more portions of the SP 105 are included within the implantable portion of the cochlear implant system 100.

The external and implantable portions of the cochlear implant system 100 may each include one or more coils configured to transmit and receive power and/or control signals via the communication link 106. For example, the external portion of the cochlear implant system 100 may include an external coil (not shown) and the implantable portion of the cochlear implant system 100 may include an implantable coil (not shown). The external coil and the implantable coil may be inductively coupled to each other, thereby allowing data to be transmitted therebetween. The data may include, for example, the magnitude and polarity of a sensed acoustic signal. The external coil may also transmit power from the external portion to the implantable portion of the cochlear implant system 100. It will be noted that, in some embodiments, both the SP 105 and the ICS 107 may be implanted within the patient, either in the same housing or in separate housings. If the SP 105 and the ICS 107 are in the same housing, the communication link 106 may be realized with a direct wire connection within such housing. If the SP 105 and the ICS 107 are in separate housings, the communication link 106 may include one or more inductive links, for example.

Figure 2:
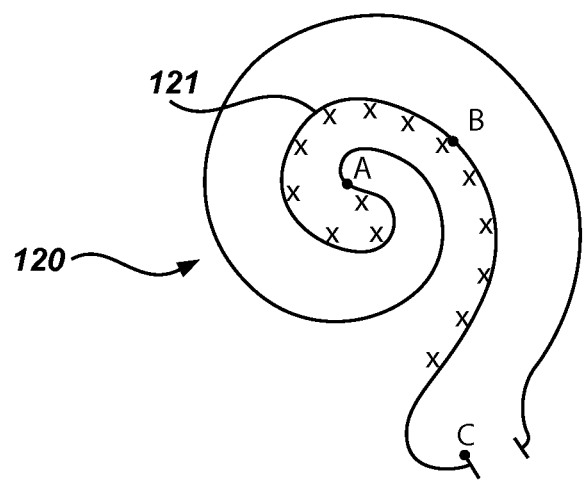
FIG. 2 illustrates a schematic structure of human cochlea according to principles described herein.

Referring to FIG. 2, there is shown a schematic structure of the human cochlea 120. The section of the cochlea 120 from point A to point B, i.e., section AB, has a spiral shape. In contrast, the section from point B to point C, i.e., section BC, is almost straight. The area of stimulation, i.e., the location of the spiral ganglion cells, is marked with X's and is separated from the duct of the cochlea 120 by the modiolar wall 121. As described previously, it is often desirable for the electrodes 109 to be positioned in close proximity to the spiral ganglion cells.

Figure 3:
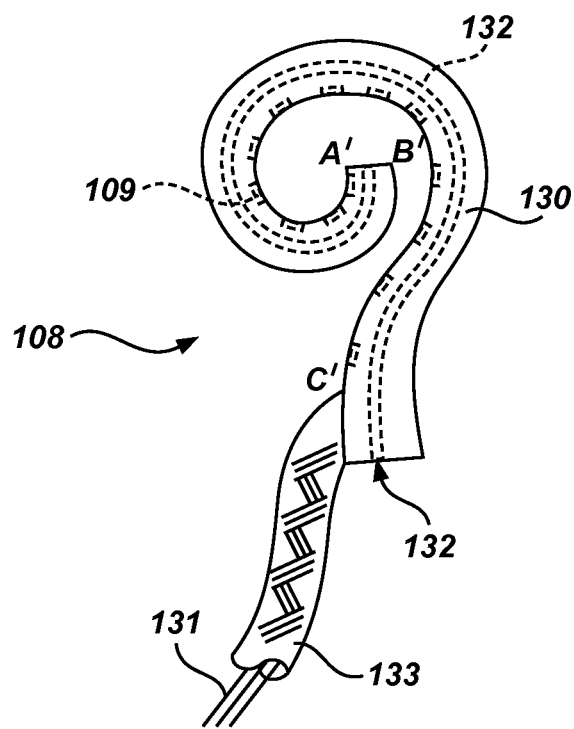
FIG. 3 illustrates an exemplary pre-curved electrode array according to principles described herein.

To this end, a pre-curved electrode array 108 is provided as shown in FIG. 3. The electrode array 108 may be substantially as shown and described in U.S. Pat. Nos. 4,819,647, 6,129,753, or 6,604,283, each of which is incorporated herein by reference in its respective entirety.

As shown in FIG. 3, the pre-curved array 108 has the same general curvature as that of the cochlea 120. In some examples, the array 108 includes an elongate flexible carrier 130 having an array of electrode contacts 109 connected to corresponding insulated wires 131. The elongate flexible carrier 130 may be made out of any suitable material such as, but not limited to, silastic, silicone rubber, or plastic and has a hole or lumen 132 passing therethrough. In some examples, the carrier 130 is constructed so as to have a built-in bias or memory force which forces the carrier 130 to naturally assume the spiral or curved shape shown in FIG. 3. In addition, the material of the carrier 130 is also configured to allow the carrier 130 to be straightened when loaded on a stylet. Once inserted within the duct of the cochlea 120, the memory force of the carrier 130 forces the carrier 130 to return to the desired curvature, e.g., as shown in FIG. 3.

As shown in FIG. 3, the wires 131 exit the carrier 130 near a proximal end thereof and form a cable 133 that connects with the ICS 107. The ICS 107 is thus able to make electrical connection with each of the electrode contacts 109 through one or more of the wires 131.

In some examples, the electrode contacts 109 of the array 108 are configured to be positioned along the medial electrode wall following the line between points A', B' and C'. This line, as shown in FIG. 3, is along a portion of the curve or spiral that is generally concave.

As mentioned, the pre-curved electrode array 108 often has to be loaded onto a stylet before the array 108 can be implanted within a duct of the cochlea. In the examples given herein, the stylet is coupled to or a part of an insertion tool. However, it will be recognized that a stand-alone stylet may alternatively be used in connection with the systems and methods described herein.

Figure 4:
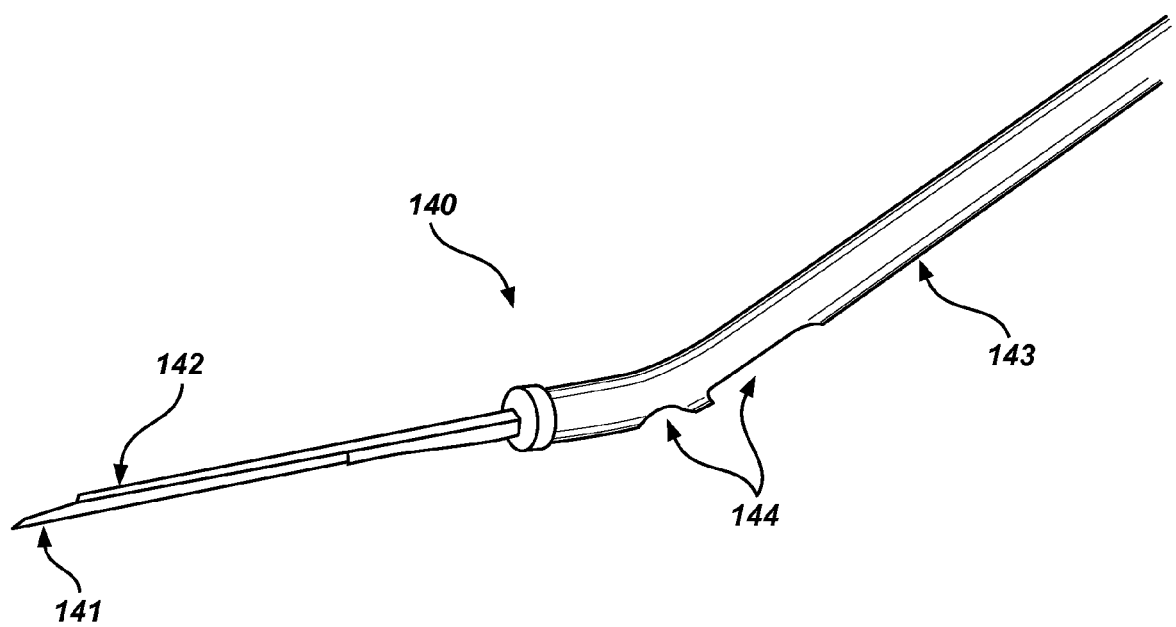
FIG. 4 is a perspective view of an exemplary insertion tool that may be used to insert a pre-curved electrode array into a duct of the cochlea according to principles described herein.

FIG. 4 is a perspective view of an exemplary insertion tool 140 that may be used to insert the pre-curved electrode array 108 into a duct of the cochlea. It will be recognized that the insertion tool 140 shown in FIG. 4 is merely exemplary and that many different variations thereof may be used in connection with the methods and systems described herein.

As shown in FIG. 4, the insertion tool 140 includes a stylet 141 and a guiding assembly 142 each coupled at a proximal end to an elongate handle 143. The stylet 141, as will be described in more detail below, has a tapered distal tip and is configured to be inserted within the lumen 132 of electrode array 108. The guiding assembly 142 runs parallel to the stylet 141 and is configured to assist in guiding the stylet 141 and electrode array 108 into a duct of the cochlea. Both the stylet 141 and guiding assembly 142 may be made out of any suitable material with sufficient stiffness so as to facilitate entry into the cochlea. For example, the stylet 141 and/or guiding assembly 142 may be made out of a metal, a metal alloy, a hard plastic, or any other suitable material.

As shown in FIG. 4, the handle 143 may extend at a bent angle from where it is coupled to the stylet 141 and guiding assembly 143 to facilitate a more convenient handling or holding thereof. In some examples, as will be described in more detail below, the handle 143 may include one or more notches 144 or other types of coupling members or devices to facilitate coupling thereof to a loading tool. The handle 143 may be made out of any suitable material as may serve a particular application.

Figure 5:
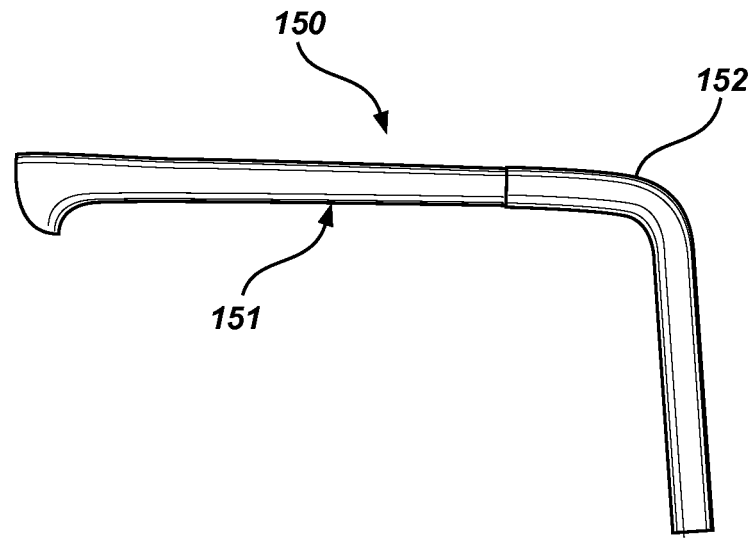
FIG. 5 illustrates an exemplary loading tool that is often used to load a pre-curved array onto the stylet of an insertion tool according to principles described herein.

FIG. 5 illustrates an exemplary loading tool 150 that is often used to load the pre-curved array 108 onto the stylet 141 of an insertion tool 140. As shown in FIG. 5, the loading tool 150 includes a tube 151 with an elongate hollow lumen extending therethrough 151. The tube 151 is coupled at one of its ends to a bent handle 152.

The hollow tube 151 includes an opening at both of its ends to allow passage therethrough of the electrode array 108 and stylet 141. The tube 151 has a length at least as long as the length of the pre-curved array 108 in a straightened state.

In some examples, the electrode array 108 is inserted into the lumen of the tube 151 prior to being loaded onto the stylet 141 of the insertion device 140. Ideally, the diameter of the lumen is such that the electrode array 108 becomes substantially straight as it is inserted therein. The stylet 141 may then be inserted into the lumen 132 of the electrode array 108.

Figure 6:
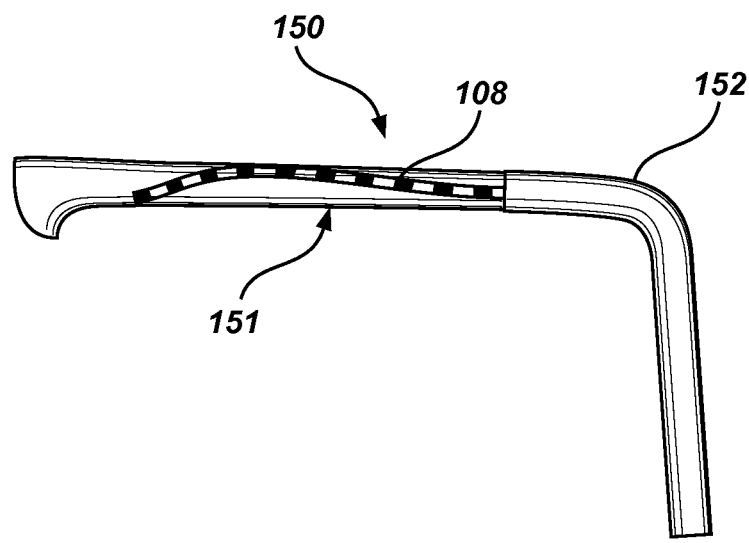
FIG. 6 shows an exemplary pre-curved electrode array that has been inserted into the lumen of the loading tool of FIG. 5 according to principles described herein.

However, because the electrode array 108 has a tendency to assume its pre-curved shaped, the electrode array 108 is often not completely straight within the lumen of the tube 151. For example, FIG. 6 shows an exemplary pre-curved electrode array 108 that has been inserted into the lumen of the loading tool 150 of FIG. 5. As shown in FIG. 6, the electrode array 108 has a wave-type shape and is not completely straight. Hence, the stylet 141 may puncture the electrode array's lumen 132 or otherwise cause damage to the electrode array 108 when inserted into the electrode array's lumen 132.

Figure 7A:
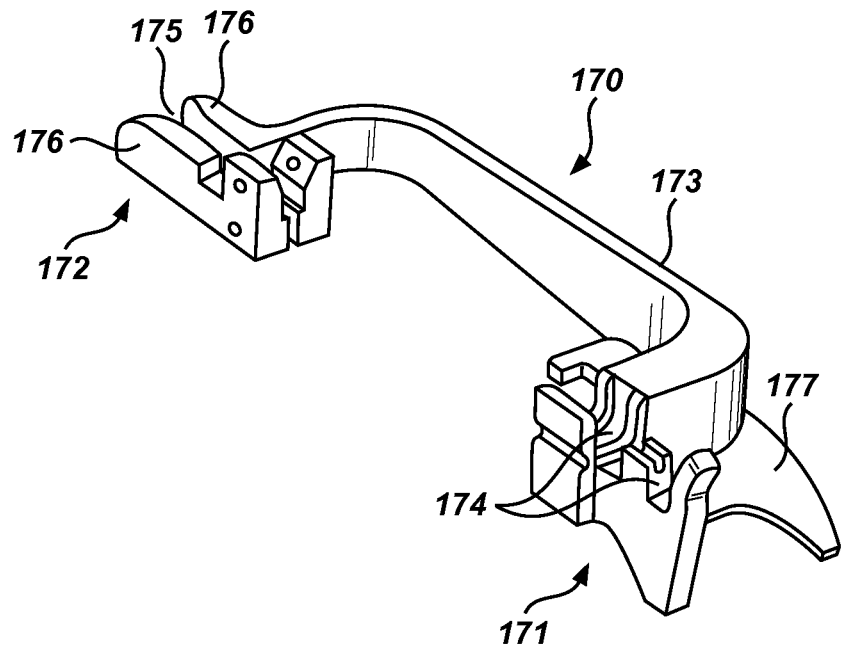
FIG. 7A is a perspective view of a loading tool configured to facilitate the loading of a pre-curved electrode array onto a stylet of an insertion tool according to principles described herein.
Figure 7B:
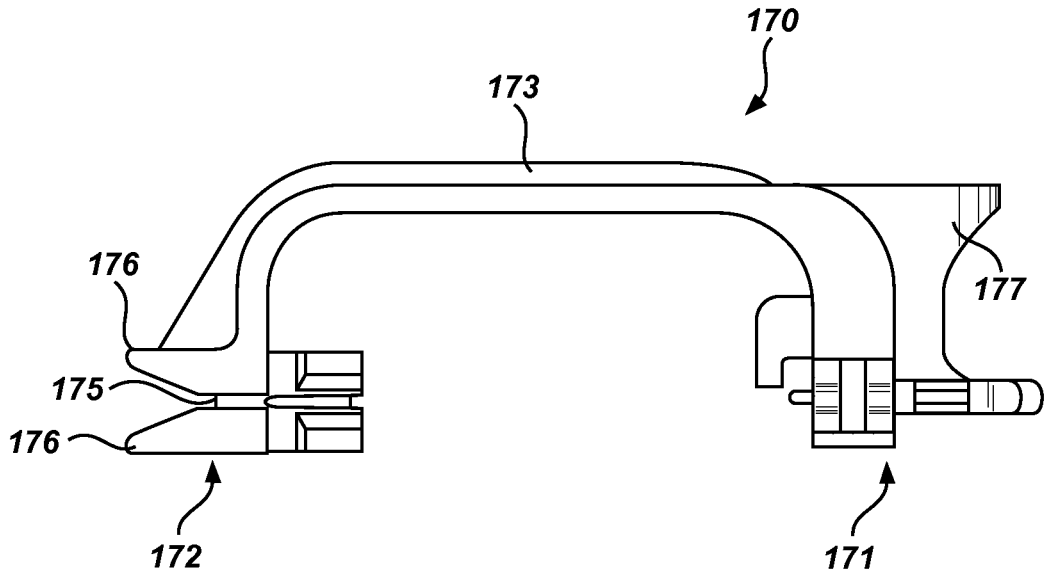
FIG. 7B is a top view of the loading tool shown in FIG. 7A according to principles described herein.

Hence, in some examples, a loading tool may be provided that does not require the electrode array 108 to be completely straightened prior to being loaded onto a stylet 141. FIG. 7A is a perspective view of a loading tool 170 configured to facilitate the loading of a pre-curved electrode array 108 onto a stylet 141 of an insertion tool 140. FIG. 7B is a top view of the loading tool 170 shown in FIG. 7A. As will be described in more detail below, the loading tool 170 allows a surgeon or other user thereof to load a pre-curved electrode array 108 onto a stylet 141 without first having to completely straighten the pre-curved electrode array 108.

As shown in FIG. 7A, the loading tool 170 may include a docking assembly 171, a channel assembly 172, and a c-shaped connecting member 173 extending therebetween. Each of these components will be described in more detail below. It will be recognized that the loading tool 170 shown in FIGS. 7A-7B is merely illustrative of the many different loading tools that may be used in connection with the methods and systems described herein. Alternative loading tools that may be used will be described in more detail below.

The docking assembly 171, as shown in FIG. 7A, is located at a proximal end of the loading tool 170 and includes one or more notches 174 configured to mate with the notches 144 in the handle 143 of the insertion tool 140. In this manner, as will be described in more detail below, the insertion tool 140 may be set or docked within the docking assembly 171.

In some examples, the docking assembly 171 may also include one or more flanges 177 configured to facilitate handling of the loading tool 170. The flanges 177 may have any suitable shape and size as may serve a particular application.

As shown in FIGS. 7A-7B, the channel assembly 172 includes a channel 175 extending therethrough. The channel 172 is uncovered from the top and may have any suitable depth as may serve a particular application. As will be described in more detail below, the pre-curved electrode array 108 may be placed within and pulled through the channel 172 to load the array 108 onto the stylet 141. Hence, the channel 172 may have any suitable width that allows for placement of the pre-curved electrode 108 therein. In some examples, the top distal corner of the channel 172 is curved or rounded so as to facilitate easier passage of the pre-curved electrode 108 therethrough.

The channel 175, as more easily seen in FIG. 7B, is aligned linearly with the docking assembly 171. In this manner, as will be described in more detail below, a distal portion of the stylet 141 may be located within at least a portion of the channel 175 when the insertion tool 140 is docked with the docking assembly 171 of the loading tool 170.

As shown in FIGS. 7A-7B, the channel assembly 172 may further include wall members 176 on either side of the channel 175. The wall members 176 may be configured to prevent the electrode array 108 from moving laterally within the channel 175. As seen more easily in FIG. 7B, the distal ends of the wall members 176 may be angled or tapered away from the distal end of the channel 175. In this manner, the wall members 176 may be further configured to guide the electrode array 108 into the channel 175 as the electrode array 108 is being pulled therethrough.

The c-shaped connecting member 173, as shown in FIGS. 7A-7B, is configured to connect the docking assembly 171 to the channel assembly 172. It will be recognized that the connecting member 173 may have any alternative shape as may serve a particular application.

In some examples, one or more of the components of the loading tool 170 may be made out of any biocompatible material as may serve a particular application. For example, the loading tool 170 may be made out of polysulfone, plastic, or metal. In some examples, the loading tool 170 is made out of a material that can be sterilized.

As shown in FIGS. 7A-7B, the loading tool 170 may be made out of a single mold. In this manner, the loading tool 170 may be manufactured using any suitable plastic injection molding process. Alternatively, as will be described in more detail below, the components of the loading tool 170 may be coupled together using any other method.

Figure 8A:
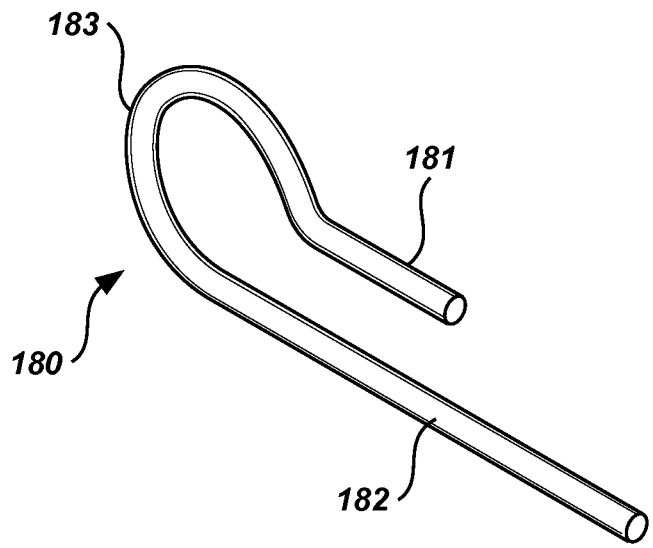
FIG. 8A is a perspective view of an exemplary retainer clip according to principles described herein.
Figure 8B:
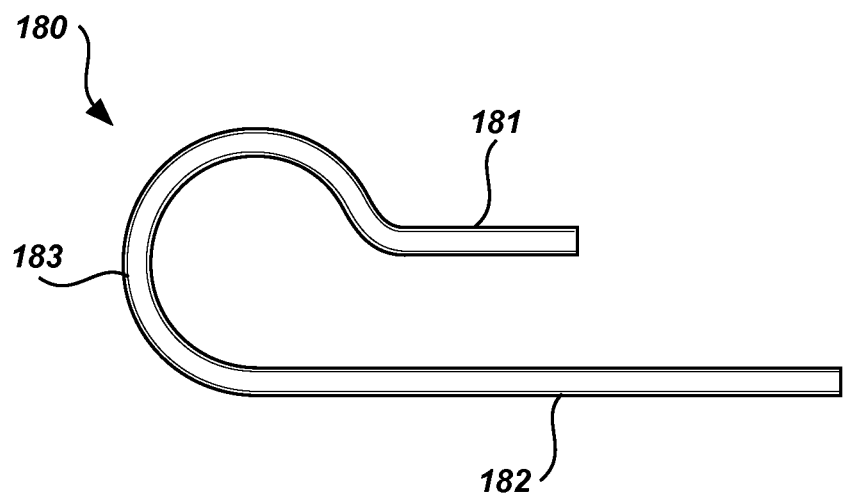
FIG. 8B is a side view of the retainer clip of FIG. 8A according to principles described herein.

In some examples, a retainer clip or other securing device or mechanism may be provided to secure the stylet 141 within the channel 175. FIG. 8A is a perspective view of an exemplary retainer clip 180 and FIG. 8B is a side view of the retainer clip 180 of FIG. 8A. As shown in FIGS. 8A-8B, the retainer clip 180 may include two substantially straight members 181 and 182 with a curved member 183 positioned therebetween. The straight members 181 and 182 are configured to be inserted into corresponding holes located within the loading tool 170. In some examples, as will be described in more detail below, the bottom straight member 182 is longer than the top straight member 181. The curved member 180 is configured to be used as a handle for a surgeon or other user. It will be recognized that the retainer clip 180 shown in FIGS. 8A-8B is merely exemplary and that any other type of retainer clip or securing device may additionally or alternatively be used to secure the stylet 141 within the channel 175.

Figure 9A:
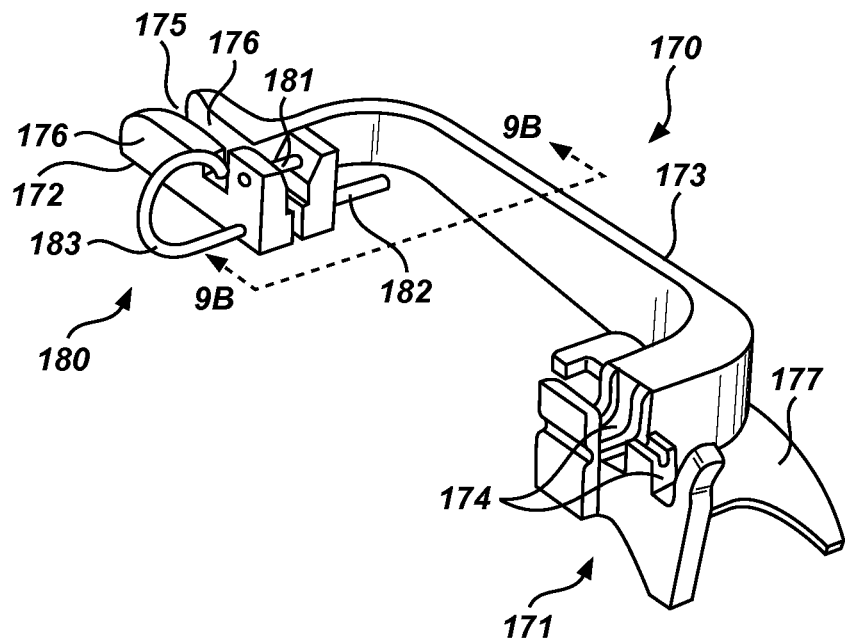
FIG. 9A is a perspective view of the retainer clip inserted into the channel assembly of the loading tool according to principles described herein.
Figure 9B:
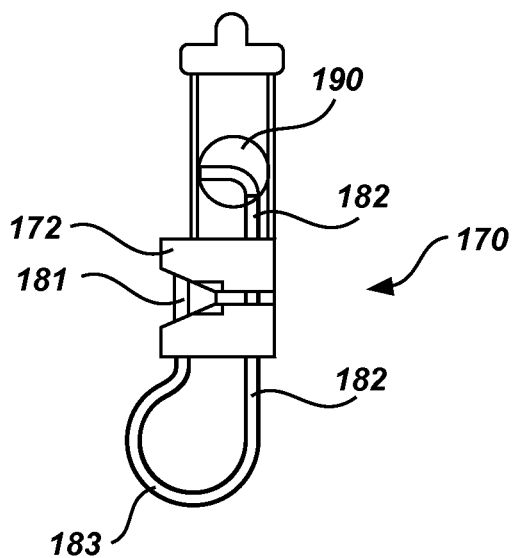
FIG. 9B is a cross sectional view of the retainer clip inserted into the channel assembly taken along the perspective line indicated in FIG. 9A.

FIG. 9A is a perspective view of the retainer clip 180 inserted into the channel assembly 172 of the loading tool 170. FIG. 9B is a cross sectional view of the retainer clip 180 inserted into the channel assembly 172 taken along the perspective line indicated in FIG. 9A. As shown in FIGS. 9A-9B, the straight members 181 and 182 of the retainer clip 180 are inserted into corresponding holes that pass laterally through the channel assembly 172. The holes are positioned such that the top member 181 is above the channel 175 and the bottom member 182 is beneath the channel 175.

As shown in FIGS. 9A-9B, the distal end 190 of the bottom straight member 182 may be bent at an angle after it is inserted within the channel assembly 172. In this manner, the retainer clip 180 may be prevented from completely coming out of the channel assembly 172 if pulled too far.

Hence, to place and secure the stylet 141 within the channel 175 of the channel assembly 170, the retainer clip 180 is first disengaged or pulled away from the channel assembly 175 until the shorter top member 181 of the retainer clip 180 does not cover the channel 175. The stylet 141 may then be placed within the channel 175. The retainer clip 180 may then be engaged or pushed through the holes in the channel assembly 170 until the top member 181 covers a portion of the stylet 141 that is within the channel 175.

An exemplary method of loading the pre-curved electrode array 108 onto a stylet 141 of an insertion tool 140 will now be described in connection with FIGS. 10A-10E. It will be recognized that the steps illustrated in FIGS. 10A-10E are merely exemplary and that they may be reordered, modified, or otherwise varied as may serve a particular application.

Figure 10A:
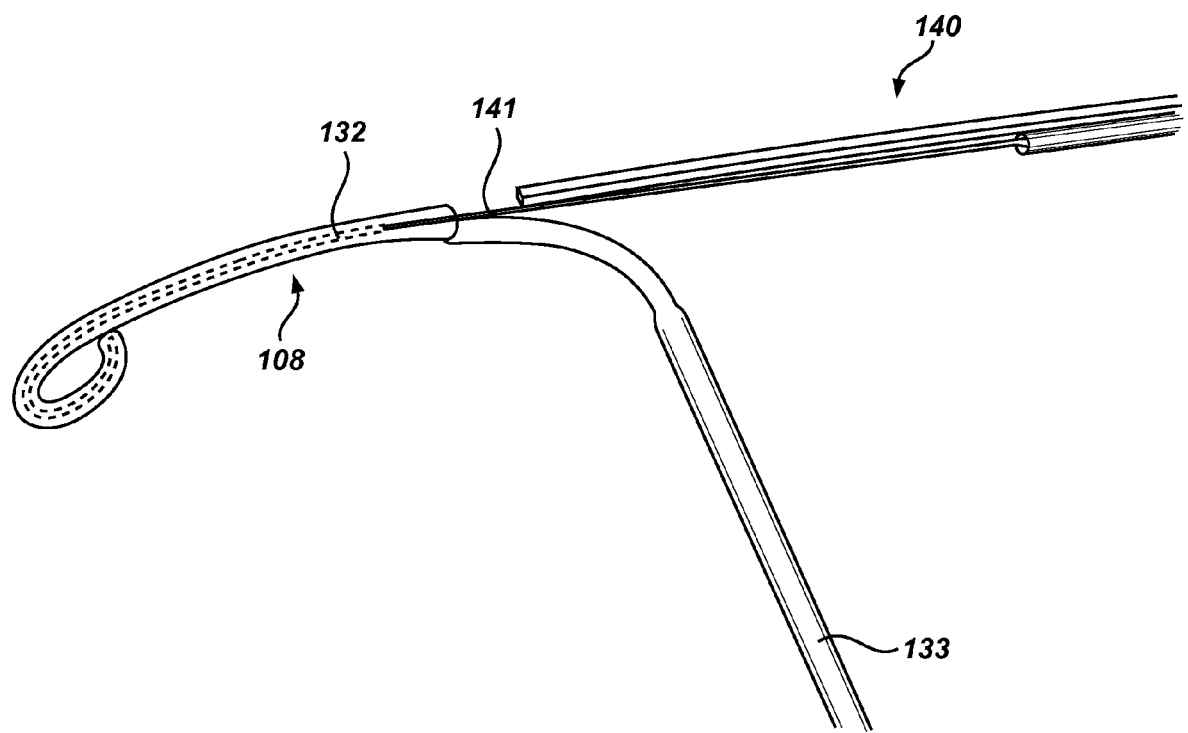
FIGS. 10A-10E illustrate an exemplary method of loading a pre-curved electrode array onto a stylet of an insertion tool according to principles described herein.

As shown in FIG. 10A, the distal portion of the stylet 141 is first inserted into a proximal portion of the lumen 132 of the electrode array 108. In some examples, as shown in FIG. 10A, the proximal portion of the lumen 132 into which the stylet 141 is inserted is relatively straight.

Figure 10B:
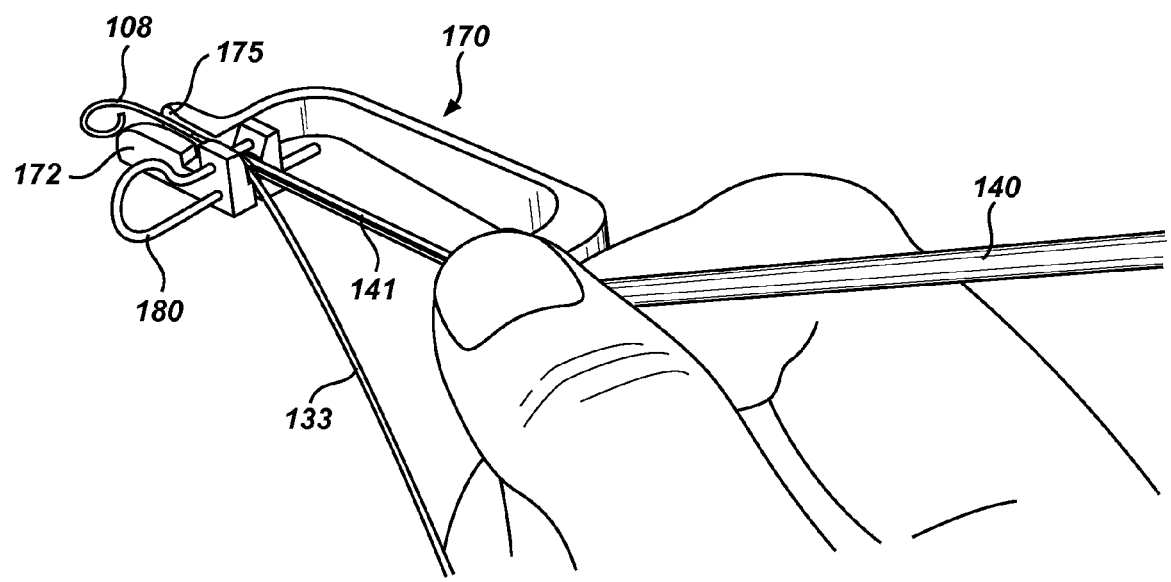

Next, as shown in FIG. 10B, the insertion tool 140 is placed within the loading tool 170. As shown in FIG. 10B, the insertion tool 140 may be placed such that the notches 144 thereof are aligned with the notches 174 of the loading tool 170. Moreover, the insertion tool 140 is placed such that the distal tip of the stylet 141 and the proximal portion of the electrode array 108 are located within the channel 175 of the loading tool 170.

Figure 10C:
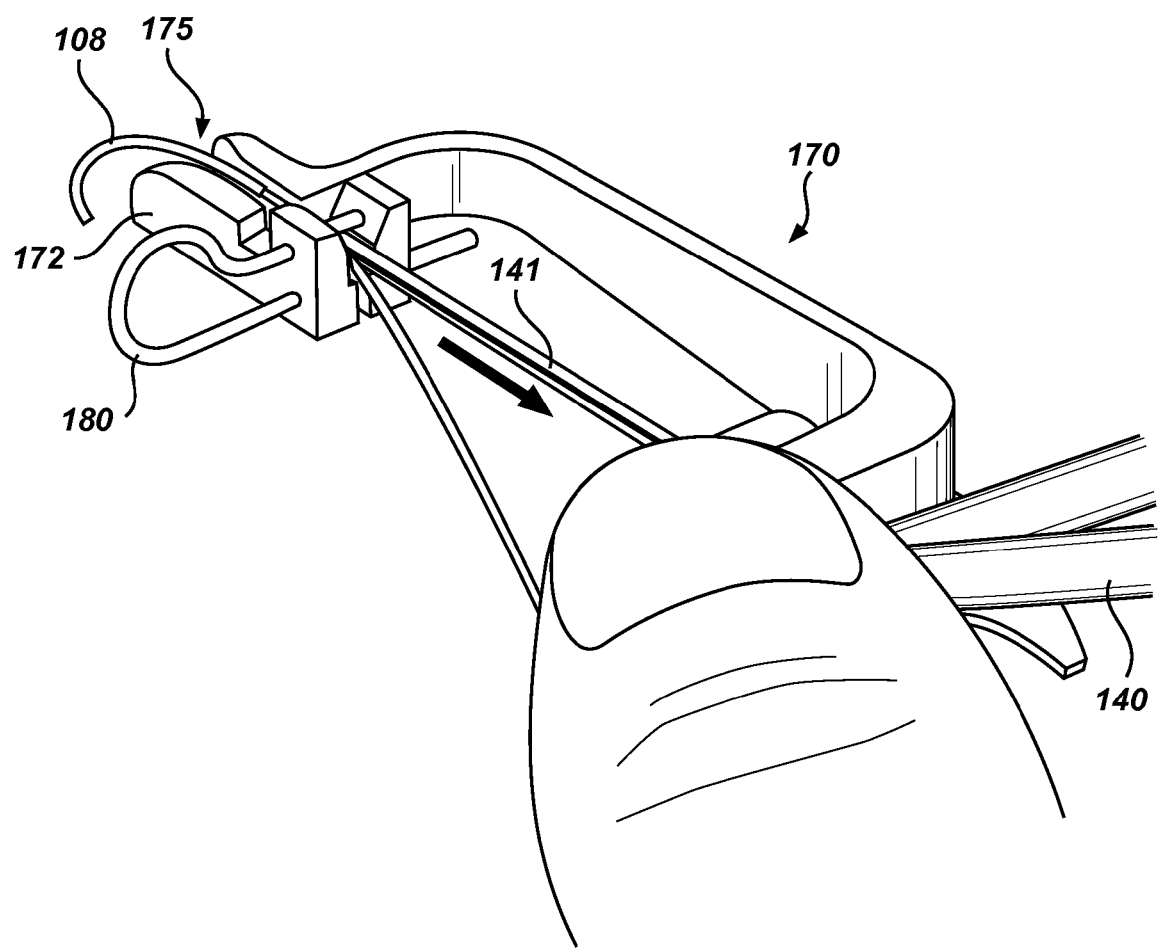

As shown in FIG. 10C, the retainer clip 180 may then be engaged to secure the distal portion of the stylet 141 within the channel 175. Once the stylet 141 has been secured within the channel 175, the surgeon or other user may load the electrode array 108 onto the stylet 141 by pulling the cable 133 of the electrode array 108 in a direction indicated by the arrow shown in FIG. 10C. As the cable 133 is pulled, the pre-curved portion of the electrode array 108 enters the channel 145 and is loaded onto the stylet 141. In this manner, the electrode array 108 does not have to be completely straightened prior to being loaded onto the stylet 141.

Figure 10D:
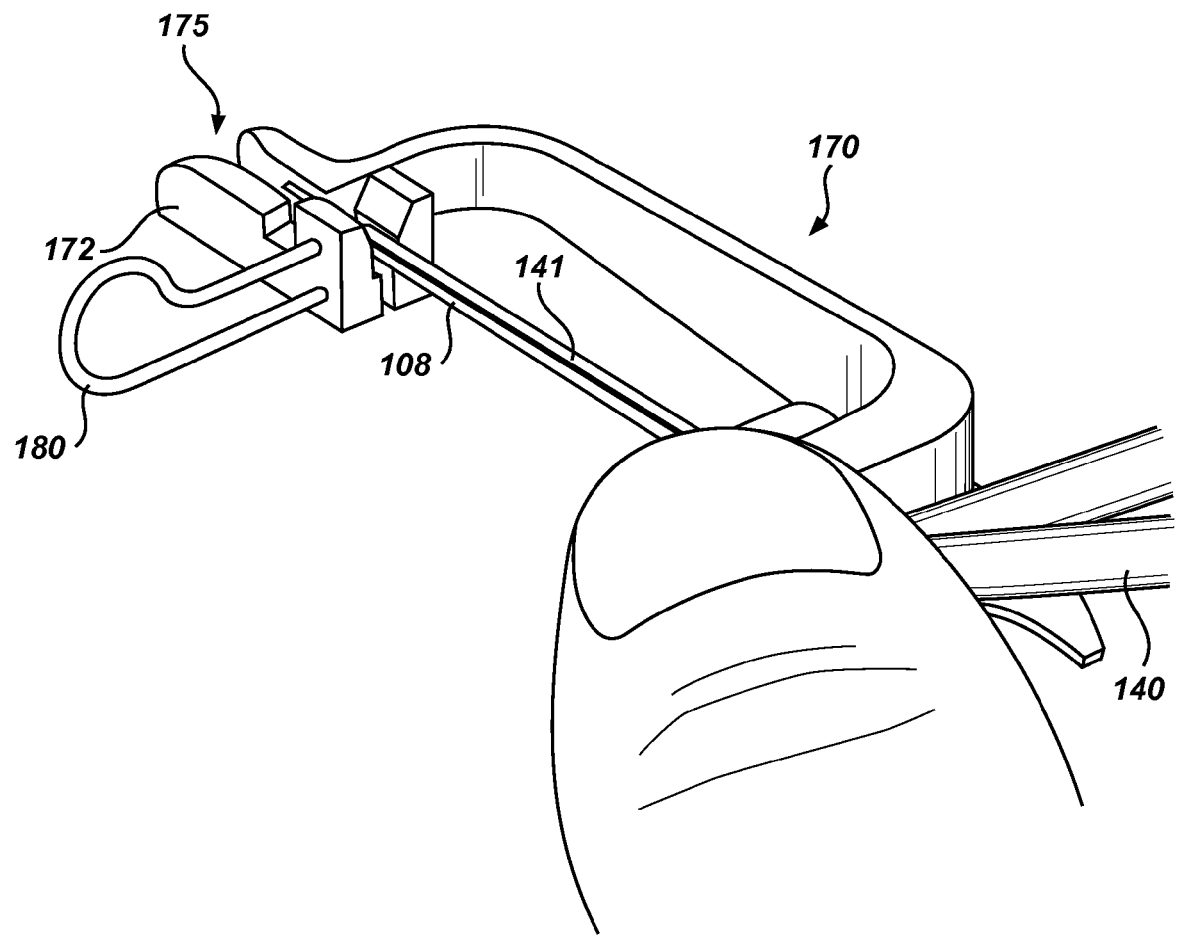
Figure 10E:
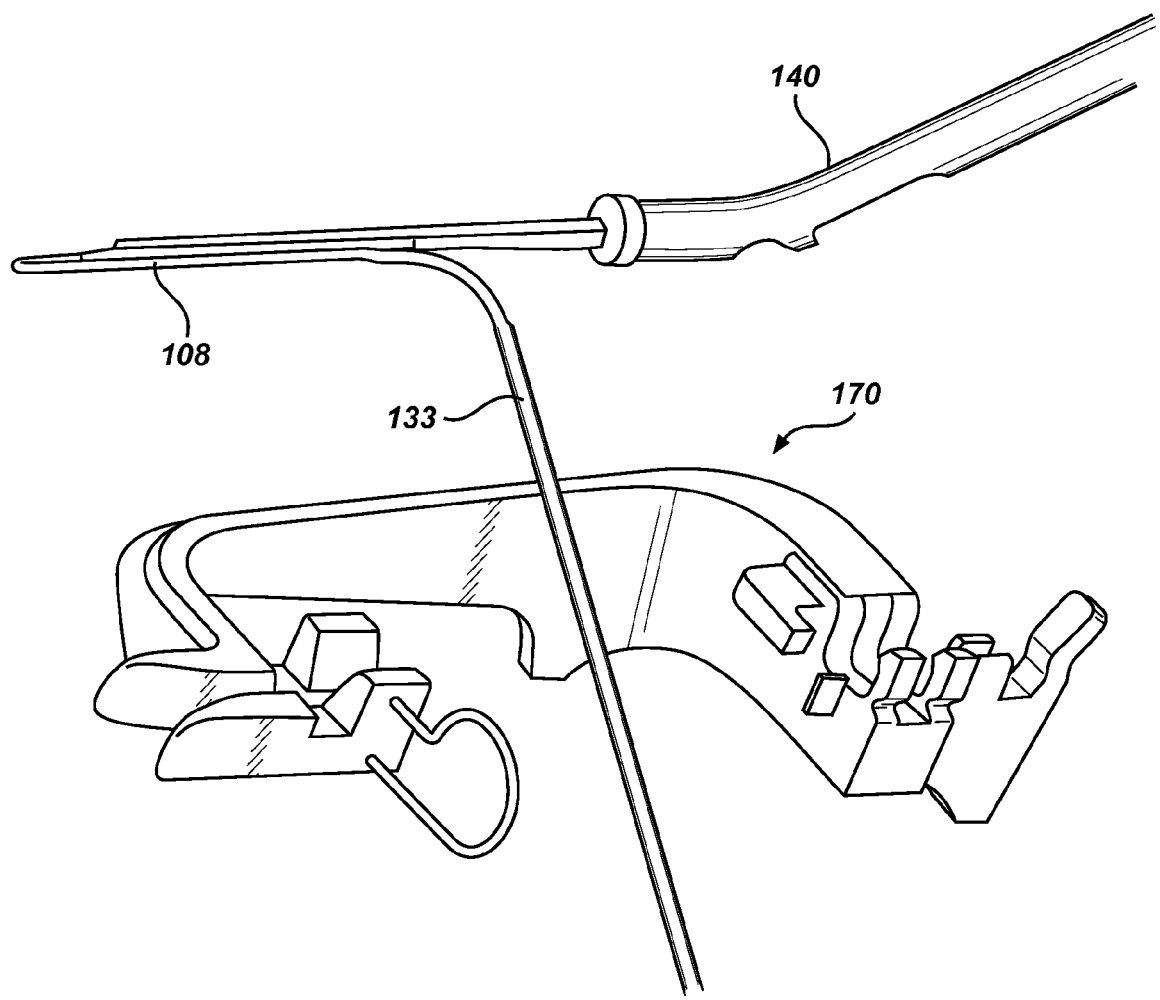

After the electrode array 108 has been loaded onto the stylet 141, the retainer clip 180 may be disengaged from the channel assembly 172, as shown in FIG. 10D. The insertion tool 140 may then be removed from the loading tool 170, as shown in FIG. 10E. As shown in FIGS. 10D-10E, the stylet 141 has been completely inserted within the lumen 132 of the electrode array 108. The electrode array 108 may then be inserted within a duct of the cochlea using any suitable insertion procedure.

Figure 11:
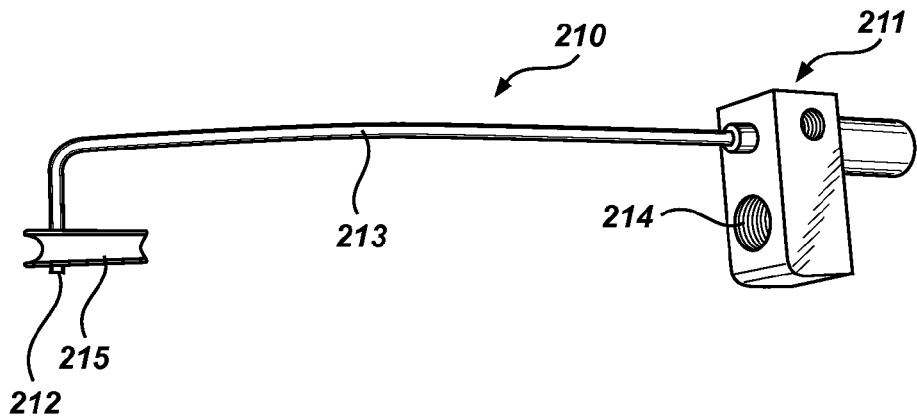
FIG. 11 is a perspective view of an alternative loading tool according to principles described herein.

FIG. 11 is a perspective view of an alternative loading tool 210 that may be used in connection with the methods and systems described herein. The loading tool 210 also includes a docking assembly 211, a channel assembly 212 and a connecting member 213.

As shown in FIG. 11, the docking assembly 211 is located at a proximal end of the loading tool 210 and includes a lumen 214 extending therethrough. As will be described in more detail below, the insertion tool 140 may be inserted through the lumen 214 of the docking assembly 211 and coupled thereto.

The channel assembly 212 includes a channel guide 215. The channel guide 215 serves a similar purpose to that of the channel 175 described in connection with FIGS. 7A-7B and is configured to allow for placement of the pre-curved electrode 108 therein. The channel guide 215 is curved so as to facilitate easier passage of the pre-curved electrode 108 therethrough.

Figure 12:
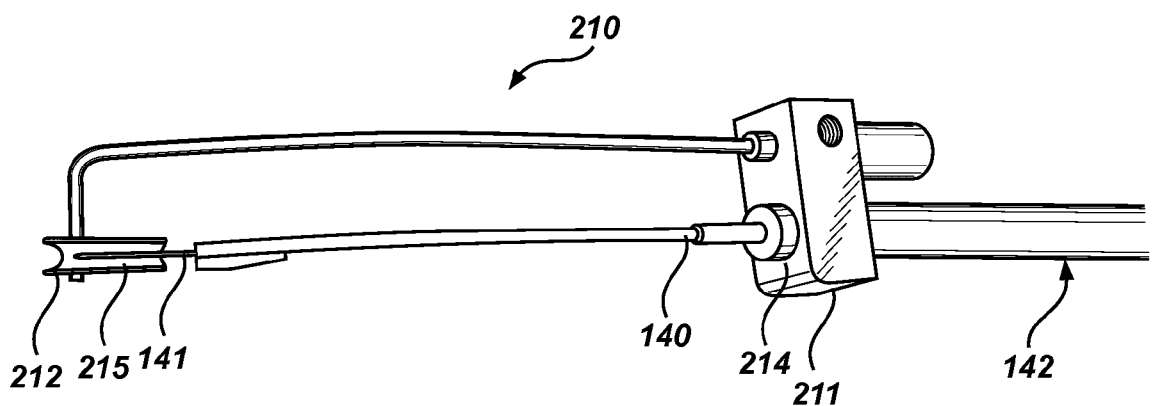
FIG. 12 is a perspective view of an insertion tool coupled to the loading tool of FIG. 11 according to principles described herein.

As shown in FIG. 11, the channel guide 215 is aligned linearly with the lumen 214 of the docking assembly 211. In this manner, a distal portion of the stylet 141 may be placed within at least a portion of the channel guide 215 when the insertion tool 140 is docked with the docking assembly 211 of the loading tool 210. For example, FIG. 12 is a perspective view of an insertion tool 140 coupled to the loading tool 210 of FIG. 11. As shown in FIG. 12, a distal portion of the stylet 141 is located within the channel guide 215. In this manner, the electrode array 108 may be loaded onto the stylet 141 in a manner similar to that described in connection with FIGS. 10A-10E.

It will be recognized that one or more of the components of the loading tool 210 shown in FIG. 11 may be made out of any biocompatible material as may serve a particular application. For example, the loading tool 210 may be made out of polysulfone, plastic, or metal. In some examples, the loading tool 210 is made out of a material that can be sterilized.

Figure 13A:
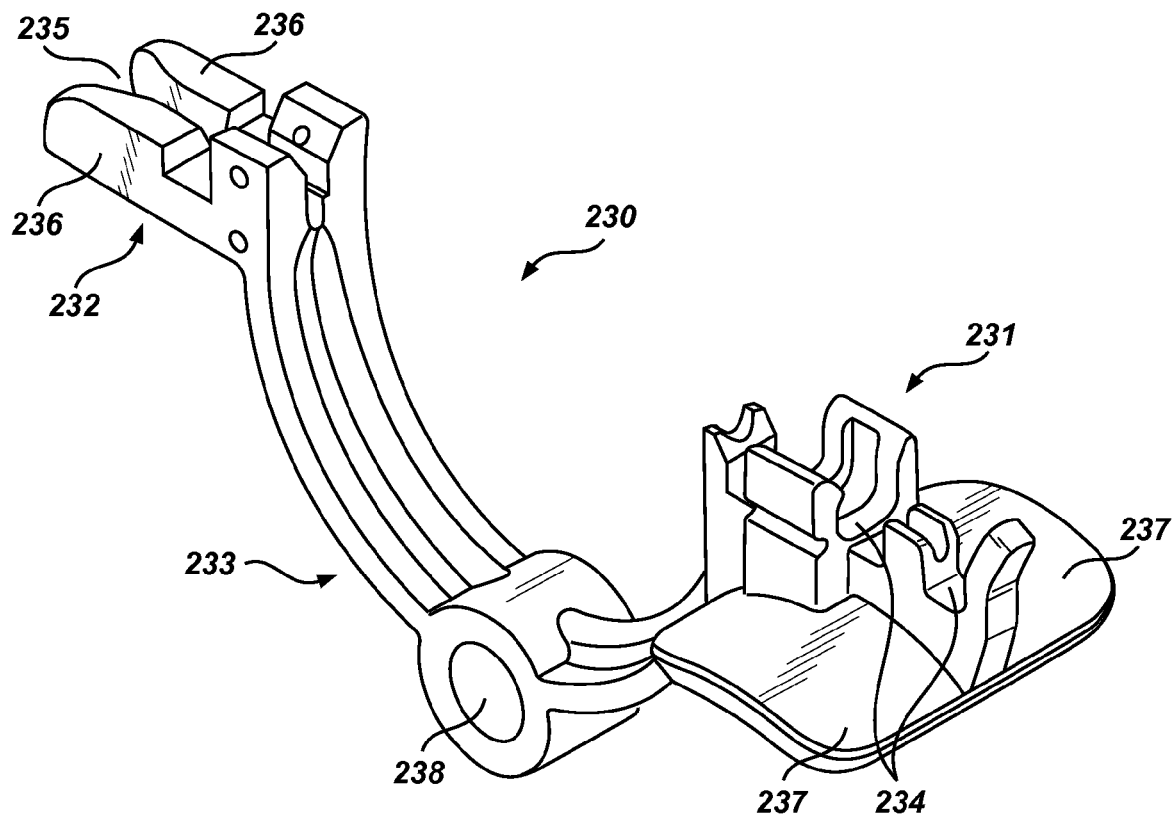
FIG. 13A is a perspective view of an alternative loading tool configured to facilitate the loading of a pre-curved electrode array onto a stylet of an insertion tool according to principles described herein.
Figure 13B:
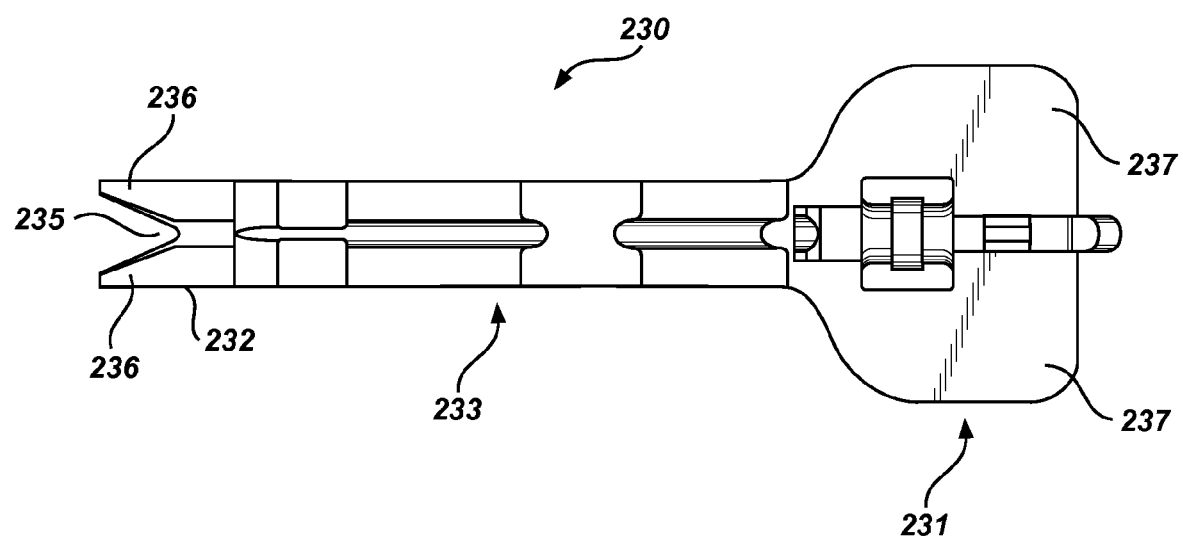
FIG. 13B is a top view of the loading tool shown in FIG. 13A according to principles described herein.

FIG. 13A is a perspective view of an alternative loading tool 230 that may be used in connection with the methods and systems described herein. FIG. 13B is a top view of the loading tool 230 shown in FIG. 13A.

As shown in FIG. 13A, the loading tool 230 may include a docking assembly 231, a channel assembly 232, and a connecting member 233 extending therebetween. Each of these components will be described in more detail below.

The docking assembly 231, as shown in FIG. 13A, is located at a proximal end of the loading tool 230 and includes one or more notches 234 configured to mate with the notches 144 in the handle 143 of the insertion tool 140. In this manner, the insertion tool 140 may be set or docked within the docking assembly 231.

In some examples, the docking assembly 231 may also include one or more flanges 237 configured to facilitate handling of the loading tool 230. The flanges 237 may have any suitable shape and size as may serve a particular application. In some examples, one or more of the flanges 237 may include laser etched wording.

As shown in FIGS. 13A-13B, the channel assembly 232 includes a channel 235 extending therethrough. The channel 235 is uncovered from the top and may have any suitable depth as may serve a particular application. As will be described in more detail below, the pre-curved electrode array 108 may be placed within and pulled through the channel 235 to load the array 108 onto the stylet 141. Hence, the channel 235 may have any suitable width that allows for placement of the pre-curved electrode 108 therein. In some examples, the top distal corner of the channel 235 is curved or rounded so as to facilitate easier passage of the pre-curved electrode 108 therethrough.

The channel 235, as more easily seen in FIG. 13B, is aligned linearly with the docking assembly 231. In this manner, a distal portion of the stylet 141 may be located within at least a portion of the channel 235 when the insertion tool 140 is docked with the docking assembly 231 of the loading tool 230.

As shown in FIGS. 13A-13B, the channel assembly 232 may further include wall members 236 on either side of the channel 235. The wall members 236 may be configured to prevent the electrode array 108 from moving laterally within the channel 235. As seen more easily in FIG. 13B, the distal ends of the wall members 236 may be angled or tapered away from the distal end of the channel 235. In this manner, the wall members 236 may be further configured to guide the electrode array 108 into the channel 235 as the electrode array 108 is being pulled therethrough.

The connecting member 233, as shown in FIGS. 13A-13B, is configured to connect the docking assembly 231 to the channel assembly 232. In some examples, the connecting member 233 includes a finger grip 238 configured to facilitate easier handling thereof. The finger grip 238 may include a lumen extending therethrough, as shown in FIG. 13A. Additionally or alternatively, the finger grip 238 may include any other structure as may serve a particular application.

In some examples, one or more of the components of the loading tool 230 may be made out of any biocompatible material as may serve a particular application. For example, the loading tool 230 may be made out of polysulfone, plastic, or metal. In some examples, the loading tool 230 is made out of a material that can be sterilized.

As shown in FIGS. 13A-13B, the loading tool 230 may be made out of a single mold. In this manner, the loading tool 230 may be manufactured using any suitable plastic injection molding process. Alternatively, as will be described in more detail below, the components of the loading tool 230 may be coupled together using any other method.

Figure 14:
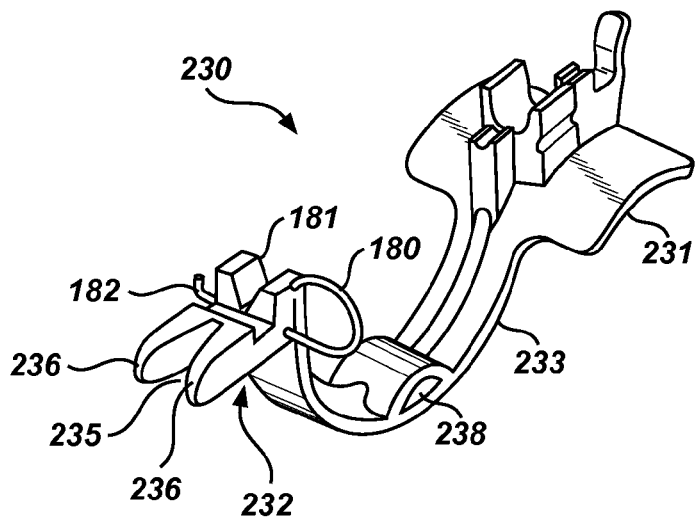
FIG. 14 is a perspective view of the retainer clip inserted into the channel assembly of the loading tool described in connection with FIGS. 13A-13B according to principles described herein.

In some examples, the retainer clip 180 described hereinabove or other securing device or mechanism may be provided to secure the stylet 141 within the channel 235. FIG. 14 is a perspective view of the retainer clip 180 inserted into the channel assembly 232 of the loading tool 230 described in connection with FIGS. 13A-13B. As shown in FIG. 14, the straight members 181 and 182 of the retainer clip 180 are inserted into corresponding holes that pass laterally through the channel assembly 232. The holes are positioned such that the top member 181 is above the channel 235 and the bottom member 182 is beneath the channel 235.

As shown in FIG. 14, the distal end 190 of the bottom straight member 182 may be bent at an angle after it is inserted within the channel assembly 232. In this manner, the retainer clip 180 may be prevented from completely coming out of the channel assembly 232 if pulled too far.

Hence, to place and secure the stylet 141 within the channel 235 of the channel assembly 230, the retainer clip 180 is first disengaged or pulled away from the channel assembly 235 until the shorter top member 181 of the retainer clip 180 does not cover the channel 235. The stylet 141 may then be placed within the channel 235. The retainer clip 180 may then be engaged or pushed through the holes in the channel assembly 230 until the top member 181 covers a portion of the stylet 141 that is within the channel 235.

Figure 15:
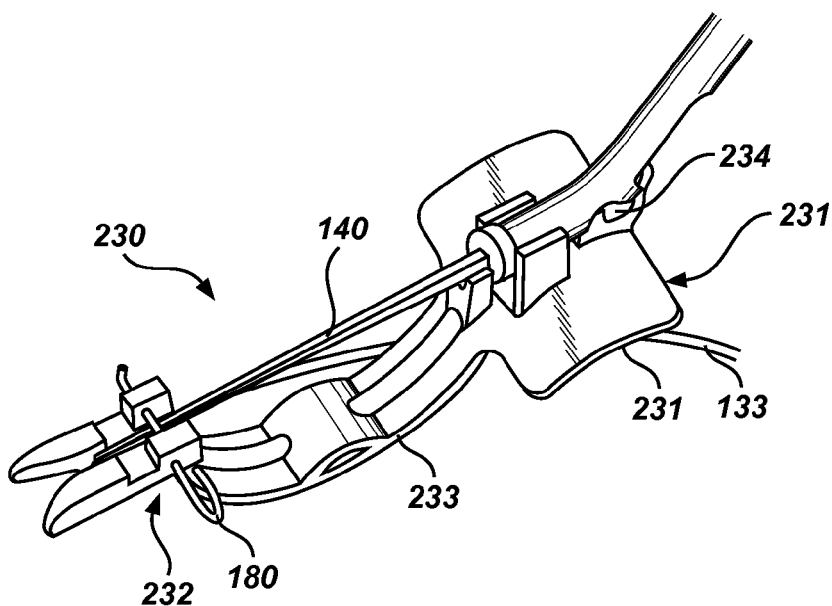
FIG. 15 is a perspective view of the loading tool described in connection with FIGS. 13A-13B with the insertion tool placed therein according to principles described herein.

FIG. 15 is a perspective view of the loading tool 230 with the insertion tool 140 placed therein. As shown in FIG. 15, the insertion tool 140 may be placed such that the notches 144 thereof are aligned with the notches 234 of the loading tool 230. Moreover, the insertion tool 140 is placed such that the distal tip of the stylet 141 and the proximal portion of the electrode array 108 are located within the channel 235 of the loading tool 230.

Figure 16:
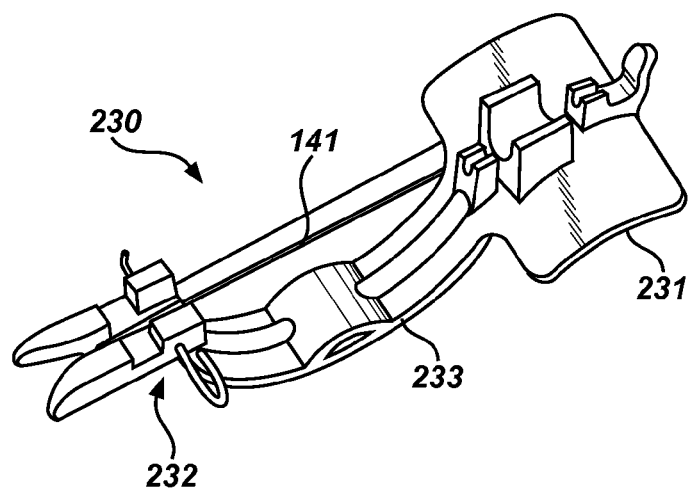
FIG. 16 shows the loading tool described in connection with FIGS. 13A-13B with the insertion tool removed therefrom according to principles described herein.

Once the stylet 141 has been secured within the channel 235 of the loading tool 230, the surgeon or other user may load the electrode array 108 onto the stylet 141 in a manner similar to that described hereinabove. The insertion tool 140 may then be removed from the loading tool 230. FIG. 16 shows the loading tool 230 with the insertion tool 140 removed therefrom.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
   a stylet associated with an insertion tool; and
   a loading tool configured to facilitate loading of a pre-curved electrode array onto said stylet, said loading tool comprising:
   a docking assembly that couples to said stylet;
   a channel assembly comprising a channel that receives and allows passage therethrough of said pre-curved electrode array; and
   a connecting member connecting to and integrally formed with said channel assembly and said docking assembly and that maintains a permanently fixed distance therebetween;
   wherein said channel of said channel assembly is aligned with said docking assembly such that when said stylet is coupled to said docking assembly, said stylet is located at least partially within said channel.

2. The system of claim 1, further comprising:
   a retainer clip coupled to said channel assembly and movable between a first position that secures said stylet within said channel and a second position that allows removal of said stylet from said channel.

3. The system of claim 1, wherein said stylet is permanently attached or configured to selectively couple to said insertion tool.

4. The system of claim 3, wherein said docking assembly comprises one or more notches that mate with one or more corresponding features of said insertion tool.

5. The system of claim 1, wherein said docking assembly comprises one or more flanges that facilitate handling of said loading tool.

6. The system of claim 1, wherein said connecting member comprises a c-shaped connecting member.

7. The system of claim 1, wherein said connecting member comprises a finger grip.

8. The system of claim 1, wherein said channel assembly further comprises one or more wall members that prevent said electrode array from moving laterally within said channel.

9. The system of claim 1, wherein said loading tool is made out of at least one of a plastic and a metal.

10. A method comprising:
    providing a stylet;
    providing a loading tool having a docking assembly configured to couple to said stylet and prevent longitudinal movement of said stylet relative to said loading tool and a channel assembly that comprises a channel configured to receive and allow passage therethrough of a pre-curved electrode array;
    inserting a distal tip of said stylet into a proximal portion of a lumen within said electrode array;
    coupling said stylet to said docking assembly such that said distal tip of said stylet is located at least partially within said channel; and
    advancing said electrode array in a proximal direction relative to said insertion tool and said stylet such that said electrode array moves through said channel and is loaded onto said stylet.

11. The method of claim 10, wherein said step of advancing said electrode array comprises pulling a proximal portion of said electrode array relative to said loading tool and said stylet.

12. The method of claim 10, wherein said channel is configured to at least partially straighten said electrode array as said electrode array is advanced.

13. The method of claim 10, further comprising securing said distal tip of said stylet within said channel.

* * * * *